United States Patent
Lang et al.

Patent Number: 6,153,180
Date of Patent: Nov. 28, 2000

[54] AGENT AND METHOD FOR PERMANENTLY SHAPING THE HAIR, BASED ON N-BRANCHED-CHAIN ALKYL-SUBSTITUTED MERCAPTO ACETAMIDES AND PROCESS FOR THEIR PREPARATION

[75] Inventors: Guenther Lang, Reinheim; Beate Dannecker, Darmstadt; Wolfgang Hanefeld, Marburg/Lahn; Heiko Walther, Marburg, all of Germany

[73] Assignee: Wella Aktiengesellschaft, Darmstadt, Germany

[21] Appl. No.: 09/142,576

[22] PCT Filed: Dec. 9, 1997

[86] PCT No.: PCT/EP97/06860

§ 371 Date: Sep. 10, 1998

§ 102(e) Date: Sep. 10, 1998

[87] PCT Pub. No.: WO98/30197

PCT Pub. Date: Jul. 16, 1998

[30] Foreign Application Priority Data

Jan. 11, 1997 [DE] Germany .......................... 197 00 725

[51] Int. Cl.⁷ .............................. A61K 7/09; A61K 31/16
[52] U.S. Cl. ............................ 424/70.5; 514/613
[58] Field of Search ............. 424/70.5; 514/613

[56] References Cited

U.S. PATENT DOCUMENTS 5,061,483  10/1991  Tieckelmann et al. .

FOREIGN PATENT DOCUMENTS

| 0 455 457 A2 | 11/1991 | European Pat. Off. . |
| 948 186 | 8/1956 | Germany . |
| 972 424 | 7/1959 | Germany . |
| 91/10421 | 7/1991 | WIPO . |

*Primary Examiner*—Diana Dudash
*Assistant Examiner*—Alysia Berman
*Attorney, Agent, or Firm*—Michael J. Striker

[57] ABSTRACT

The subject of the invention is an agent for the permanent shaping of hair, characterized in that it contains as active keratin-reducing substance a compound in accordance with the general formula

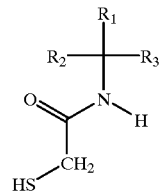

(I)

in which $R_1$, $R_2$ and $R_3$ stand for H, carboxy or a straight- or branched-chain alkyl radical, monohydroxyalkyl radical or polyhydroxyalkyl radical with 1 to 6 carbon atoms respectively, on the condition that not all radicals $R_1$ to $R_3$ stand for H at the same time;

if $R_1$ and $R_2$ stand for H, then $R_3$ is carboxy or a branched alkyl, branched monohydroxyalkyl or branched polyhydroxyalkyl radical with 1 to 6 carbon atoms;

if none of the radicals $R_1$ to $R_2$ stand for carboxy or have a branched alkyl, branched monohydroxyalkyl or branched polyhydroxyalkyl radical with 1 to 6 carbon atoms, then at least two of the radicals $R_1$, $R_2$ or $R_3$ stand for a straight-chain alkyl, monohydroxyalkyl or polyhydroxyalkyl radical with 1 to 6 carbon atoms and if one of the radicals is carboxy, then the other two radicals are not carboxy at the same time.

The agent allows for gentle, even shaping of the hair in a way that protects the skin and the hair, at a pH range of 6.5 to 9.5, without causing allergic and sensitizing reactions.

10 Claims, No Drawings

AGENT AND METHOD FOR PERMANENTLY SHAPING THE HAIR, BASED ON N-BRANCHED-CHAIN ALKYL-SUBSTITUTED MERCAPTO ACETAMIDES AND PROCESS FOR THEIR PREPARATION

BACKGROUND OF THE INVENTION

1. Field of the Invention

The present invention relates to an agent for the permanent shaping of hair containing certain new mercaptoacetamides as an active keratin-reducing substance and to a method for the permanent shaping of hair using such substances.

2. Prior Art

It is known that the classical method for achieving a permanent shaping of the hair is based on two treatment steps: In the first step, the cystine-disulfide bridges of the hair keratin are opened by means of the action of an agent containing an active reducing substance (shaping agent). The hair is then shaped into the desired form. In a second step, the cystine-disulfide bonds are closed again by means of a fixing agent, i.e. an agent containing oxidizing substances.

In classical reducing agents for permanent shaping, as shown by the pioneering work in German patent applications 948 186 and 972 424, thioglycolic acid is used, for example in the form of ammonium salt or monoethanolamine salt. Other classically used active substances are inorganic sulfites, 2-mercaptopropionic acid (thiolactic acid), 3-mercaptopropionic acid, certain mercaptocarboxylic acid esters, cysteine, and derivatives of these compounds.

All these agents, however, have a number of disadvantages. Despite being effective enough, preparations based on mercaptocarboxylic acids and adjusted to be alkaline cause hair damage, which is expressed for example in increased breakage of the hair. Often these substances also place undesirable stress on the scalp.

Finally, the unpleasant odor of the reducing agents used requires an intensive addition of scent to the product. By using 2-mercaptopropionic acid (thiolactic acid) it is possible to solve some of the aforementioned problems. However, in comparison to thioglycolic acid which is generally used, the shaping achieved with thiolactic acid is limper.

Mercaptocarboxylic acid esters that make the shaping of hair possible even at low pH values are not satisfactory in terms of their tolerance by the skin and their risk of sensitization. In place of mercaptocarboxylic acid esters, mercaptocarboxylic acid amides such as thioglycolic acid amide or alkyl- or hydroxyalkyl-substituted amides have also been also used. Such compounds are known from international patent application WO-A-91/10421 and European patent application EP-A-0 455 457. These substances, like carboxylic acid esters, have a high shaping potential even at low pH values, but with regard to sensitization, they are even more critical than the esters.

SUMMARY OF THE INVENTION

It has now surprisingly been discovered that the aforementioned disadvantages can be avoided by using the aforementioned mercaptoacetamides based on the branched-chain amines in accordance with the invention, and that they have a stronger shaping potential than thiolactic acid.

The subject of the present invention is therefore an agent for permanently shaping the hair, characterized in that, as an active keratin-reducing substance, it contains a compound of the general formula:

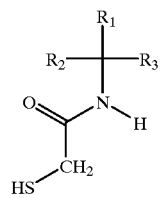
(I)

in which $R_1$, $R_2$ and $R_3$ stand for H, carboxy or a straight- or branched-chain alkyl radical, monohydroxyalkyl radical or polyhydroxyalkyl radical with 1 to 6 carbon atoms respectively, on the condition that not all radicals $R_1$ to $R_3$ stand for H at the same time;

if $R_1$ and $R_2$ both stand for H, then $R_3$ is carboxy or a branched alkyl, monohydroxyalkyl or polyhydroxyalkyl radical with 1 to 6 carbon atoms;

if none of the radicals $R_1$ to $R_2$ stand for carboxy or a branched alkyl, monohydroxyalkyl or polyhydroxyalkyl radical with 1 to 6 carbon atoms, then at least two of the radicals $R_1$, $R_2$ or $R_3$ stand for a straight-chain alkyl, monohydroxyalkyl or polyhydroxyalkyl radical with 1 to 6 carbon atoms and if one of the radicals is carboxy, then the other two radicals are not carboxy at the same time.

Preferred compounds of formula (I) are those in which $R_1$, $R_2$ and $R_3$ each stand for H, $CH_3$, $CH_2CH_3$, $CH_2CH_2CH_3$, $CH(CH_3)_2$, $C(CH_3)_3$, $CH_2CH(CH_3)CH_3$, $CH(OH)CH_3$, $CH_2OH$, $CH_2CH_2OH$, $CH_2CH(OH)CH_3$, $CH_2CH_2CH_2OH$, $CH_2CH(OH)CH_2OH$, $CH(CH_3)(CH_2OH)$, $CH(CH_2OH)_2$, or COOH.

Particularly preferred compounds are those of the formulae

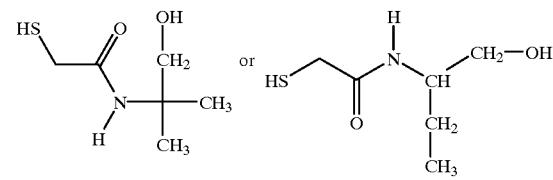

The preparation of the mercaptoacetamide in accordance with the invention is done by reacting the corresponding amines with methyl thioglycolate in a protective gas atmosphere, extraction in the proper solvent, and subsequent molecular distillation.

The mercaptoacetamides in accordance with the invention are used in the ready-to-use agents for shaping hair in a quantity of 3 to 28 weight-%, preferably 5 to 21 weight-%.

The mercaptoacetamides in accordance with the invention can also be used in further embodiments of the invention in a mixture of other known thiols, such as thioglycolic acid, thiolactic acid, cysteine, cysteamine and alkyl- or acylcysteamines or sulfites.

The ready to use hair shaping agents preferably have a pH value of 6.9 to 9.5, particularly preferred is 6.5 to 8.5. As alkalizing agent or an agent for adjusting the pH value, ammonia or caustic lye of soda can particularly be considered, but also all other water-soluble, physiologically tolerable salts of organic and inorganic bases, such as ammonium hydrogen carbonate.

The shaping agent can be offered as a single or two-component package. If it is in two-component form, the two components are mixed immediately prior to use. The preparation can either be available in form of an aqueous solution or emulsion or in a water-based thickened form, particularly as a cream, gel, mousse or paste.

It is understood that the shaping agent can contain all known additives customary for these type of preparations, for example thickeners, such as bentonite, fatty acids, starch, polyacrylic acid and their derivatives, cellulose derivatives, alginates, vaseline, paraffin oils; wetting agents or emulsifiers in the category of anionic, cationic, amphoteric or non-ionic surfactants, such as fatty alcohol sulfates, fatty alcohol ether sulfates, alkyl sulfonates, alkyl benzene sulfates, quaternary ammonium salts, alkyl betaines, ethoxylated alkyl phenols, fatty acid alkanolamides, or ethoxylated fatty acid esters; in addition opacifiers, for example polyethylene glycol ester; alcohols, such as ethanol, propanol, isopropanol and glycerin; sugar, for example D-glucose; solubilizers, stabilizers, buffer substances, perfume oils, pigments as well as hair conditioning and hair care components, for example cationic polymers, lanolin derivatives, cholesterol, pantothenic acid, and betaine.

The aforementioned components are used in the appropriate quantity commonly employed for these purposes, for example the wetting agents and emulsifiers in concentrations of a total of 0.2 to 30 weight-%; the alcohols in a quantity of a total of 0.1 to 20 weight-%; the opacifiers, perfume oils and pigments in a quantity of 0.01 to 1 weight-% each; the buffer substances in a total quantity of 0.1 to 10 weight-%; and sugar, solubilizers, stabilizers, as well as hair conditioning and hair care components in a quantity 0.1 to 5 weight-% each, while the thickeners and solvents can be contained in this preparation in a total quantity of 0.5 to 20 weight-%.

Further, for increased effectiveness, so-called swelling and penetration substances can be added to this preparation, as for example dipropylene glycol monomethyl ether, 2-pyrrolidone or 2-imidazolidinone, in a quantity of 1 to 30 weight-%, as well as dithio compounds to prevent excessive frizzing of the hair, for example dithiodiglycolic acid, dithiolactic acid, the dithiols of the compounds of formula (I), or the respective salts of the dithiols.

By varying the pH value, with added heat penetration if necessary, an agent can be made available which is universally suitable for every hair texture. The agent creates a flexible, permanent, even shaping from the hairline to the hair ends without causing allergic or sensitizing reactions.

The present invention further relates to a method for the permanent shaping of hair, by which the hair, before or after it is set into the desired form, is treated with the shaping agent, rinsed with water and then treated oxidatively, rinsed with water, if necessary set in a water wave and then dried, which is characterized in that the aforementioned substances in accordance with the invention are employed as the shaping agents.

In a preferred embodiment of the method of the invention, the hair is first washed with a shampoo and then rinsed with water. Next, the towel-dried hair is divided up into individual strands and wound onto curlers with a diameter of 5 to 30 millimeters, preferably 5 to 15 millimeters. The hair is then treated with a quantity of the described shaping preparation according to the invention, preferably 60 to 120 grams, that suffices for shaping the hair.

After a sufficient action time necessary for the permanent shaping, which can last 5 to 30 minutes (10 to 30 minutes without heat penetration; 5 to 20 minutes with heat penetration) depending on the consistency of the hair, the pH value and the shaping efficiency of the shaping agent, as well as the temperature applied, the hair is rinsed with water and then oxidatively post-treated ("fixed"). The post-treatment agent, depending on the hair volume, preferably is used in a quantity of 80 to 100 grams.

For the oxidative post-treatment in a rolled or unrolled state any suitable post-treatment agent for this type of treatment can be used. Examples of oxidation agents used in such post-treatment preparations are potassium- and sodium bromate, sodium perborate, carbamide peroxide and hydrogen peroxide. The concentration of the oxidation agent depends on the applied time frame (as a rule 5 to 15 minutes) and the different temperature applied. Normally the oxidation agent in the ready-to-use aqueous post-treatment agent is present in a concentration of 0.5 to 10 weight-%. The agent for the oxidative post-treatment can of course contain other substances, for example wetting agents, conditioning substances such as active cationic polymers, weak acids, buffer substances or peroxide stabilizers, and can be available in the form of an aqueous solution, an emulsifier in thickened, water-based form, particularly as a cream, gel or paste. These conventional additives can particularly be contained in the post-treatment agent at a quantity of 0.1 to 10 weight-%.

Subsequently the curlers are removed. If necessary, the unrolled hair once more can be oxidatively post-treated. Then the hair is rinsed with water, optionally set in a water wave, and finally dried.

The following examples are to explain the subject of the invention in more detail, however, without limiting the subject to these examples.

EXAMPLES

Example 1

The preparation of the new branched-chain alkyl-substituted mercaptoacetamide takes place either in accordance with Method A by means of reacting the respective primary amine with methyl thioglycolate at a temperature not to exceed 30° C., or in accordance with Method B with chloroacetyl chloride, at an initial temperature not to exceed 5° C., followed by potassium xanthogenate at room temperature. After isolation of the reaction product, purification is done, preferably by way of a molecular distillation.

The analytical results of the products of the reaction are reflected in the following Table 1.

Preparation of the mercaptoacetamides by Method A

Into a 500 ml three-necked flask, 2 mol of the respective primary amine is introduced. In a cooling process by way of a water bath, 1 mol of methyl thioglycolate is slowly added drop by drop, so that the temperature does not exceed 30° C. The starting mixture is rinsed well and stirred until the methyl thioglycolate is quantitatively caused to react (control samples by way of thin film chromatography on Merck-DC aluminum foil 5×10 cm; silica gel 60 F 254).

The mixture is acidified with 36% hydrochloric acid (pH 2–4) while being cooled with ice, and is thoroughly extracted with ethyl acetate. The solvent is distilled off in a vacuum in the forced circulation evaporator, the residue is raised to a pH 7.0 by adding caustic lye of soda and once more is extracted by shaking with ethyl acetate. The joined fractions are dried and concentrated by way of sodium sulfate. The resulting residue is distilled by way of a molecular distiller at a maximum of 0.01 Torr into its purest form possible. This method is significant for achieving a product that is as pure as possible and has a good yield. Impurities due to incomplete reactions of fission-products from thermolysis or hydrolysis due to their sensitizing characteristics can only be avoided by means of careful distillation.

Preparation of the mercaptoacetamides by Method B

In a 1-liter three-necked flask one mol of the respective primary amine is dissolved in 500 ml water (amino acids in 500 ml 1N-NaOH) and cooled down to 0° C. in an iced water bath. The solution is mixed with 250 ml 2N-NaOH, and one mol chloroacetyl chloride is added drop by drop in such a way that the temperature does not exceed 5° C. The starting mixture is stirred vigorously for three hours at room temperature. Subsequently the mixture receives one mol of potassium xanthogenate and continues to be stirred for another twelve hours at room temperature. The mixture is acidified with 36% hydrochloric acid until a yellow oil separates. This oil is separately dissolved in a mixture of 500 ml 25%-ammonia and 250 ml ethanol. It is stirred for one hour at room temperature. Then the ethanol is distilled off in a vacuum by way of a forced circulation evaporator and the residue is extracted by shaking with ethyl acetate. The aqueous phase is carefully acidified and extracted once more with ethyl acetate. The solvent is distilled off in a vacuum by way of a forced circulation evaporator; the residue finally is purified by distillation (see Method A) or is recrystallized from ethyl acetate.

TABLE 1

| Mercaptoacetamides Amine Components | Yield in % | Elementary Analysis calc./found | HPLC (Fixed Point) | Boiling Point | WSN pH = 7 | WSN pH = 8 | WSN pH = 9 | Synthesis Method |
|---|---|---|---|---|---|---|---|---|
| 1) N-(2'-Hydroxy-tert-butyl)-2-mercaptoacetamide | 74 | C: 44.15, H: 8.03 N: 8.58, S: 19.64 C: 43.75, H: 7.99 N: 8.62, S: 19.61 | 90.778 | 117° C./0.01 Torr | 81 | 98 | 102 | A |
| 2) N-2'-(1-Hydroxybutyl)-2-mercaptoacetamide | 59 | C: 44.15, H: 8.03 N: 8.58, S: 19.64 C: 44.22, H: 8.00 N: 8.36, S: 19.40 | 97.375 | 121° C./0.01 Torr | 78 | 83 | 97 | A |
| 3) N-(2'-Butyl)-2-mercaptoacetamide Isobutylamine | 85 | C: 48.95, H: 8.90 N: 9.51, S: 21.77 C: 48.61, H: 8.59 N: 9.26, S: 21.60 | 98.25 | 85° C./0.01 Torr | 79 | 88 | 96 | A |
| 4) N-[1,1-bis(Hydroxymethyl)ethyl)]-2-mercaptoacetamide 2-Amino-2-methyl-1,3-propandiol | 35 6.73 | C: 40.21, H: 7.31 N: 7.81, S: 17.89 C: 39.71, H: N: 7.77, S: 18.13 | 98.12 | Fixed point: 89° C. | 80 | 94 | 96 | A |
| 5) N-Isopropyl-2-mercaptoacetamide Isopropylamine | 70 | C: 45.08, H: 8.32 N: 10.51, S: 24.07 C: 44.96, H: 7.99 N: 10,15, S: 23.08 | 98.111 | 71° C./0.01 Torr | 78 | 74 | 98 | A |
| 6) N-tert-Butyl-2-mercaptoacetamide tert-Butytamine | 26 | C: 48.95, H: 8.90 N: 9.51, S: 21.77 C: 48.58, H: 8.61 N: 9.725, S: 22.06 | 97.13 | 62° C. | 64 | 74 | 96 | B |
| 7) N-(2-Mercaptoacetyl)-Leucine | 77 | C: 46.81, H: 7.37 N: 6.82, S: 15.62 C: 46.84, H: 7.22 N: 7.01, S: 15.70 | 96.22 | 138° C. | 53 | 68 | 69 | B |

TABLE 1-continued

| Mercaptoacetamides Amine Components | Yield in % | Elementary Analysis calc./found | HPLC (Fixed Point) | Boiling Point | WSN pH = 7 | WSN pH = 8 | WSN pH = 9 | Synthesis Method |
|---|---|---|---|---|---|---|---|---|
| 8) N-Isobutyl-2' mercaptoacetamide | 61 | C: 48.95, H: 8.90 N: 9.51, S: 21.77 | 97.95 | 97° C./0.1 | 79 | 86 | 102 | A |
| Isobutylamine | | C: 48.77, H: 8.69 N: 9.50, S: 21.69 | | | | | | |
| Thiolactic acid as comparison | | | | | 57 | 50 | 70 | |

Example 2

Preparation of N-(2'-butyl)-2-mercaptoacetamide

In a 500-ml-three-necked flask 146.26 g (2 mol) isobutylamine is introduced. Slowly 106.24 g methyl thioglycolate is added drop by drop in such a way that the temperature does not exceed 30° C. The starting mixture is rinsed well with argon and stirred for two days at room temperature.

The mixture is acidified with 36% hydrochloric acid (pH 2–4) while being cooled with ice, and is thoroughly extracted with ethyl acetate. The solvent is distilled off in a vacuum in the forced circulation evaporator, the residue is raised to a pH 7.0 by adding caustic lye of soda and once more is extracted by shaking with ethyl acetate. The joined fractions are dried and concentrated by way of sodium sulfate. The resulting residue is distilled into a pure product by way of a molecular distiller at a maximum of 0.01 Torr. The yield amounts to 125 g (85%).

Analysis:
a) $^1$H-NMR (CDCl$_3$):
  δ (ppm)=6.49 (convex, —NH)
  3.905 (m, 4H, +NH—CH)
  3.23 (d, 2H, HS—CH$_2$—CO)
  1.89 (convex, 1H, HS)
  1.505 (m, 2H, NH—CH—CH$_2$)
  1.16 (m, 3H, NH—CH—CH$_3$)
  0.92 (t, 3H, CH$_2$—CH$_3$)
b) $^{13}$C-NMR (CDCl$_3$):
  δ (ppm)=168.43 (—C=O)
  47.08 (NH—CH)
  29.51 (NH—CH—CH$_2$—CH$_3$)
  28.43 (HS—CH$_2$)
  20.32 (CH—CH$_3$)
  10.41 (CH$_2$—CH$_3$)
c) MS (70 e V, EI, RT)
  med/time (%)=(Mass$^+$)=147 (60.86)
    132 (2.26), 114 (15.61), 104 (18.59), 100 (15.26), 92 (15.41), 91 (10.39), 72 (14.51), 57 (100)
d) Thiol titration: 96.35%
e) Elementary analysis: C$_6$H$_{13}$NOS (Molecular Weight: 147.24)
  Calculated: C, 48.95, H, 8.90, N, 9.51, S, 21.77;
  Found: C, 48.61, H, 8.59, N, 9.26, S, 21.60
f) IR (NaCl-Plates): 3294s (NH)
  3075-2878s (CH$_2$)
  2555w (SH)
  1646s (N-mono-substituted amide)
  1559s (N-mono-substituted amide)
g) HPLC: The HPLC for the compound resulted in 98.25% per unit area.
  (Column: C 18 5U, 250 mm×4.6 mm; mobile phase acetonitrile:
  Buffer [4 g KH$_2$PO4+0.8 g octane sulfonic acid-Na-salt+2 ml H$_3$PO$_4$]=25:75; flow rate 0.5 ml/min; wave length 200 nm;)
h) Particle Acid Dissociation
  Constant: 7.357 (H$_2$O)
i) UV-max: 201 nm (acetonitrile: buffer-25:75)
j) Boiling Point: 95° C./0.01 Torr

Example 3

Preparation of N-(2'-hydroxy-tert-butyl)-2-mercaptoacetamide

In a 500-ml-three-necked flask 178.19 g (2 mol) 2-amino-2-methylpropanol is introduced. Slowly 106.24 g methyl thioglycolate are added drop by drop in such a way that the temperature does not exceed 30° C. The starting mixture is rinsed well with argon and stirred for two days at room temperature.

The mixture is acidified with 36% hydrochloric acid (pH 2–4) while being cooled with ice, and is thoroughly extracted with ethyl acetate. The solvent is distilled off in a vacuum in the forced circulation evaporator, the residue is raised to a pH 7.0 by adding caustic lye of soda, and extraction is done once more by shaking with ethyl acetate. The joined fractions are dried and concentrated by way of sodium sulfate. The resulting residue is distilled into a pure product by way of a molecular distiller at a maximum of 0.01 Torr. The yield is 121 g (74%).

Analysis:
a) $^1$H-NMR (CDCl$_3$):
  δ (ppm)=6.81 bs, 1H NH
  4.55 bs, 1H OH
  3.6 bs, 2H CH$_2$—OH
  3.21 s, 2H 2-H
  1.95 bs, 1H HS
  1.32 s, 6H CH$_3$
b) $^{13}$C-NMR (CDCl$_3$)
  δ (ppm)=170.07 (C-1)
  70.07 (CH$_2$—OH)
  56.17 (NH—C)
  28.77 (C-2)
  24.31 (CH$_3$)
c) MS (70 e V, EI, 50° C.)
  med/time (%)=(Mass$^+$)=163 (4, Mass$^+$)
    132 (100), 105 (100), 92 (13), 73 (28), 58 (92), 55 (17)

d) Thiol titration: 96.81% e) Elementary analysis: $C_6H_{13}NO_2S$ (Molecular Weight: 163.23 g/mol)
Calculated: C, 44.15, H, 8.03, N, 8.58, S, 19.64;
Found: C, 43.75, H, 7.99, N, 8.62, S, 19.61 f) IR (NaCl-Plates):
3304s (OH)
3084-2933m ($CH_2$)
2556w (SH)
1654s (N-mono-substituted amide)
1559s (N-mono-substituted amide)

g) HPLC: The HPLC for the compound resulted in 90.778% per unit area.
(Column: C 18 5U, 250 mm×4.6 mm; mobile phase acetonitrile:
Buffer [4 g $KH_2PO_4$+0.8 g octane sulfonic acid-Na-salt+2 ml $H_3PO_4$]=25:75; flow rate 0.5 ml/min; wave length 200 nm;)

h) particle Acid Dissociation Constant: 7.96 ($H_2O$)

i) UV-max: <207.8 nm (acetonitrile: buffer—25:75)

j) Boiling Point: 117° C./0.01 Torr

Example 4

Comparison of the Wave Strength

The wave strength of the 1-mercaptoacetamides was determined by using glycerin monothioglycolate as a control substance and with the aid of wave solutions at a pH=7, 8 and 9. For this purpose, 16.5 centimeters of long, pre-bleached and thus damaged strands of hair (each comprising about 100 hairs) of Central European origin, were rolled in wet condition onto standard spiral curlers (inside diameter: 3 millimeters) and after conditioning in a climate controlled room (temperature: 20° C.; air humidity: 65%) were treated with a solution containing 87 mmol/100 g of the reducing agent, set to the respective pH value. The quantity of wave solution applied was calculated at a ratio 1:1.2 (1 g hair: 1.2 ml waving solution). The reaction time was set for 20 minutes; the reaction temperature was 50° C. Subsequently the hair was fixed with a peroxide-containing fixative, dried and after the curlers were removed was suspended for four hours in a water bath (water bath temperature: 40° C.).

The wave stability was calculated in accordance with the following formula:

$$\text{Wave Stability in \%} = \frac{l_o - l_t}{l_o - l_1} \times 100$$

$l_o$=total length of the non-shaped, stretched strands (16.5 cm)

$l_t$=length of the unrolled, suspended strand after 240 minutes $l_1$=length of the shaped, rolled strand at an interior roller diameter of 3 mm: $l_1$=35 millimeters As a standard, small strands were treated with a glycerin monothioglycolate solution set correspondingly to a pH of 9. The standardized wave stabilities listed in Table I refer to the standard solution (pH=9), whose wave stability was set to 100%.

Table I shows that the wave strength of the mercaptoacetamide is higher at pH 7, 8 and 9 than with thiolactic acid.

Example 5

Permanent Shaping Agent for Colored Hair

| | |
|---|---|
| 12.0 g | N-(2'-Hydroxy-tert-butyl)-2-mercaptoacetamide |
| 0.4 g | Ammonia (25% aqueous solution) for adjusting the pH |
| 2.0 g | Ammonium hydrogen carbonate |
| 2.0 g | Isopropanol |
| 1.0 g | Isooctylphenol, ethoxylated with 10 mol ethylene oxide |
| 1.0 g | Poly(dimethyl diallylammonium chloride) |
| 0.3 g | perfume oil |
| 0.1 g | Mixed vinylpyrrolidone/styrene polymer (Antara 430 of GAF Corp.; New York/USA) |
| 81.2 g | Water |
| 100.0 g | |

The pH value of this agent is in the range of 7.0 to 7.5.

Color treated and thus pre-damaged hair is washed with shampoo, towel-dried and rolled onto curlers with a diameter of 8 millimeters. Subsequently, the previously described hair shaping agent is evenly applied over the rolled hair. Then the hair is covered with a plastic cap and is heated for 10 minutes under a dryer at a temperature of 45° C. Subsequently the cover is removed, the hair is rinsed with water and receives an oxidative post-treatment with 100 grams of a 3% aqueous hydrogen peroxide solution. After removal of the curlers, the hair is once again rinsed in water, set in a water wave and then dried.

The thus treated hair will possess an even, flexible and permanent shaping of the hair.

Example 6

Permanent Shaping Agent for Normal Hair

| | |
|---|---|
| 17.5 g | N-(2'-Butyl)-2-mercaptoacetamide |
| 8.9 g | Ammonia (25% aqueous solution) |
| 5.0 g | Ammonium hydrogen carbonate |
| 4.0 g | Uric acid |
| 2.4 g | Monoethanolamine |
| 1.5 g | Isooctylphenol, ethoxylated with 10 mol ethylene oxide |
| 0.5 g | Poly(dimethyl diallylammonium chloride) |
| 0.5 g | Perfume oil |
| 0.1 g | Mixed vinylpyrrolidone/styrene polymer (Antara 430 of GAF Corp.; New York/USA) |
| 59.6 g | Water |
| 100.0 g | |

The pH value of this agent is in the range of 8.4.

Normal, non-damaged hair is washed, towel-dried and rolled onto curlers with a diameter of 6 millimeters. Subsequently the hair is evenly moistened with the aforementioned hair shaping agent. After a reaction time of 15 minutes the hair is thoroughly rinsed and then receives an oxidative post-treatment with 80 grams of a 3% aqueous hydrogen peroxide solution. After removal of the curlers, the hair is rinsed once more with water, set in a water wave and finally dried. The thus treated hair possesses an even and vibrant curl.

Example 7

Permanent Shaping Agent for Normal Hair

| | |
|---|---|
| 17.5 g | N-2'(1-Hydroxybutyl)-2-mercaptoacetamide |
| 8.9 g | Ammonia (25% aqueous solution) for adjusting the pH |
| 5.0 g | Ammonium hydrogen carbonate |
| 2.0 g | D-Glucose |
| 2.4 g | Ammonia |
| 1.5 g | Isooctylphenol, ethoxylated with 10 mol ethylene oxide |
| 0.5 g | Poly(dimethyl diallylammonium chloride) |
| 0.5 g | Perfume oil |
| 0.1 g | Mixed vinylpyrrolidone/styrene polymer (Antara 430 of GAF Corp.; New York/USA) |
| 61.6 g | Water |
| 100.0 g | |

The pH value of this agent is in the range of 8.0 to 8.5.

Normal, non-damaged hair is washed, towel-dried and rolled onto curlers with a diameter of 6 millimeters. Subsequently the hair is evenly moistened with the aforementioned hair shaping agent. After a reaction time of 15–25 minutes the hair is thoroughly rinsed and then given an oxidative post-treatment with 80 grams of a 3% aqueous hydrogen peroxide solution. After the curlers are removed the hair is rinsed once more with water, set in a water wave and finally dried. The thus-treated hair has an even and vibrant curl.

What is claimed is:

1. An agent for the permanent shaping of hair, characterized in that it contains as active keratin-reducing substance a compound of the general formula

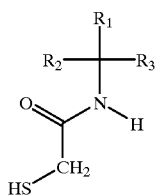

(I)

in which $R_1$, $R_2$ and $R_3$ stand for H, carboxy or a straight- or branched-chain alkyl radical, monohydroxyalkyl radical or polyhydroxyalkyl radical with 1 to 6 carbon atoms respectively, on the condition that
   not all radicals $R_1$ to R3 stand for H at the same time;
   if $R_1$ and $R_2$ stand for H, then $R_3$ is carboxy or a branched alkyl, branched monohydroxyalkyl or branched polyhydroxyalkyl radical with 1 to 6 carbon atoms;
   if none of the radicals $R_1$ to $R_2$ stand for carboxy or have a branched alkyl, branched monohydroxyalkyl or branched polyhydroxyalkyl radical with 1 to 6 carbon atoms, then at least two of the radicals $R_1$, $R_2$ or $R_3$ stand for a straight-chain alkyl, monohydroxyalkyl or polyhydroxyalkyl radical with 1 to 6 carbon atoms and
   if one of the radicals is carboxy, then the other two radicals are not carboxy at the same time.

2. The agent in accordance with claim 1, characterized in that in formula (I) $R_1$, $R_2$ and $R_3$ respectively stand for H, $CH_3$, $CH_2CH_3$, $CH_2CH_2CH_3$, $CH(CH_3)_2$, $C(CH_3)_3$, $CH_2CH(CH_3)CH_3$, $CH(OH)CH_3$, $CH_2OH$, $CH_2CH_2OH$, $CH_2CH(OH)CH_3$, $CH_2CH_2CH_2OH$, $CH_2CH(OH)CH_2OH$, $CH(CH_3)(CH_2OH)$, $CH(CH_2OH)_2$, or COOH.

3. A composition for permanent shaping of hair, said composition having a pH of from 6.5 to 8.5 and comprising:
   water;
   from 3 to 28 percent by weight of a N-branched-chain alkyl-substituted mercaptoacetamide of the formula (I):

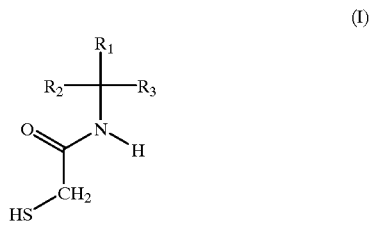

(I)

wherein $R_1$, $R_2$ and $R_3$, independently of each other, are each selected from the group consisting of H, carboxy, straight-chain alkyl radials with 1 to 6 carbon atoms, branched-chain alkyl radicals with 1 to 6 carbon atoms, straight-chain monohydroxyalkyl radicals with 1 to 6 carbon atoms, branched-chain monohydroxyalkyl radicals with 1 to 6 carbon atoms, straight-chain polyhydroxyalkyl radicals with 1 to 6 carbon atoms and branched-chain polyhydroxyalkyl radical with 1 to 6 carbon atoms,
   with the proviso that each of said $R_1$, $R_2$ and $R_3$ do not simultaneously represent said H, and if said $R_1$ and said $R_2$ both represent said H, then said $R_3$ is selected from the group consisting of said carboxy, said branched-chain alkyl radicals with 1 to 6 carbon atoms, said branched-chain monohydroxyalkyl radicals with 1 to 6 carbon atoms and said branched-chain polyhydroxyalkyl radicals having 1 to 6 carbon atoms, and
   if none of said $R_1$, $R_2$ and $R_3$ represent said carboxy or any of said branched-chain alkyl radicals with 1 to 6 carbon atoms or any of said branched-chain monohydroxyalkyl radicals with 1 to 6 carbon atoms or any of said branched-chain polyhydroxyalkyl radicals with 1 to 6 carbon atoms, then at least two of said $R_1$, $R_2$ and $R_3$ are each selected from the group consisting of said straight-chain alkyl radicals with 1 to 6 carbon atoms, said straight-chain monohydroxyalkyl radicals with 1 to 6 carbon atoms and said straight-chain polyhydroxyalkyl radicals with 1 to 6 carbon atoms, and
   if one of said $R_1$, $R_2$ and $R_3$ represents said carboxy, then remaining ones of said $R_1$, $R_2$ and $R_3$ do not represent said carboxy; and
   at least one additive ingredient selected from the group consisting of alcohols, wetting agents, emulsifiers, thickeners, opacifiers, perfume oils, pigments, buffer substances, sugars, solubilizers, stabilizers, hair conditioning ingredients and hair care ingredients.

4. The composition as defined in claim 3, containing from 0.2 to 30% by weight of at least one of said wetting agents and said emulsifiers.

5. The composition as defined in claim 3, containing an agent for adjusting pH.

6. The composition as defined in claim 5, wherein said agent for adjusting pH comprises ammonia.

7. A method for permanent shaping of hair, said method comprising the steps of:
a) putting the hair in a desired shape;
b) before and/or after the hair is put in the desired shape, applying an amount of a permanent shaping composition to the hair and allowing the permanent shaping composition to act on the hair for a predetermined acting time sufficient for the permanent shaping of the hair;
c) subsequently rinsing the hair with water;
d) performing an oxidative post-treatment of the hair;
e) after the oxidative post-treatment, rinsing the hair again with water and drying the hair;
wherein said permanent shaping composition has a pH of from 6.5 to 8.5 and comprises water and from 3 to 28 percent by weight of N-branched-chain alkyl-substituted mercaptoacetamide of the formula (I):

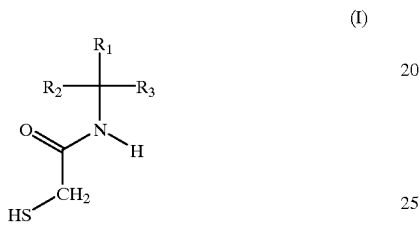

wherein $R_1$, $R_2$ and $R_3$, independently of each other, are each selected from the group consisting of H, carboxy, straight-chain alkyl radials with 1 to 6 carbon atoms, branched-chain alkyl radicals with 1 to 6 carbon atoms, straight-chain monohydroxyalkyl radicals with 1 to 6 carbon atoms, branched-chain monohydroxyalkyl radicals with 1 to 6 carbon atoms, straight-chain polyhydroxyalkyl radicals with 1 to 6 carbon atoms and branched-chain polyhydroxyalkyl radical with 1 to 6 carbon atoms, with the proviso that each of said $R^1$, $R_2$ and $R_3$ do not simultaneously represent said H, and if said R and said $R_2$ both represent said H, then said $R_3$ is selected from the group consisting of said carboxy, said branched-chain alkyl radicals with 1 to 6 carbon atoms, said branched-chain monohydroxyalkyl radicals with 1 to 6 carbon atoms and said branched-chain polyhydroxyalkyl radicals having 1 to 6 carbon atoms, and if none of said $R_1$, $R_2$ and $R_3$ represent said carboxy or any of said branched-chain alkyl radicals with 1 to 6 carbon atoms or any of said branched-chain monohydroxyalkyl radicals with 1 to 6 carbon atoms or any of said branched-chain polyhydroxyalkyl radicals with 1 to 6 carbon atoms, then at least two of said $R_1$, $R_2$ and $R_3$ are each selected from the group consisting of said straight-chain alkyl radicals with 1 to 6 carbon atoms, said straight-chain monohydroxyalkyl radicals with 1 to 6 carbon atoms and said straight-chain polyhydroxyalkyl radicals with 1 to 6 carbon atoms, and if one of said $R_1$, $R_2$ and $R_3$ represents said carboxy, then remaining ones of said $R_1$, $R_2$ and $R_3$ do not represent said carboxy.

8. The method as defined in claim 7, wherein said amount of said permanent shaping composition is 60 to 120 grams.

9. The method as defined in claim 7, wherein said acting time is from 5 to 30 minutes.

10. The method as defined in claim 7, further comprising heating during said allowing of said permanent shaping composition to act on the hair and wherein said acting time is from 5 to 20 minutes.

* * * * *